US008852081B2

(12) United States Patent
Beadle

(10) Patent No.: US 8,852,081 B2
(45) Date of Patent: Oct. 7, 2014

(54) AMUSEMENT DEVICE

(71) Applicant: Michael T. Beadle, Mandeville, LA (US)

(72) Inventor: Michael T. Beadle, Mandeville, LA (US)

( * ) Notice: Subject to any disclaimer, the term of this patent is extended or adjusted under 35 U.S.C. 154(b) by 134 days.

(21) Appl. No.: 13/657,355

(22) Filed: Oct. 22, 2012

(65) Prior Publication Data

US 2013/0165748 A1 Jun. 27, 2013

Related U.S. Application Data

(60) Provisional application No. 61/550,268, filed on Oct. 21, 2011.

(51) Int. Cl.
*A61F 5/00* (2006.01)
*A61H 23/02* (2006.01)
*A61H 19/00* (2006.01)

(52) U.S. Cl.
CPC ........ *A61H 19/40* (2013.01); *A61H 2201/1635* (2013.01); *A61H 23/02* (2013.01); *A61H 19/00* (2013.01); *A61H 19/50* (2013.01)
USPC .............................................................. 600/38

(58) Field of Classification Search
USPC ......... 600/38–41; 128/845; 602/5, 19, 32–33, 602/36
See application file for complete search history.

(56) References Cited

U.S. PATENT DOCUMENTS

| | | | |
|---|---|---|---|
| 4,343,299 | A | 8/1982 | Oxendine, Jr. |
| 4,430,990 | A | 2/1984 | Whitehead |
| 4,524,760 | A | 6/1985 | Lerner |
| 6,604,526 | B1 | 8/2003 | Coward |
| D622,031 | S | 8/2010 | Wyszynski |
| 2003/0145861 | A1 | 8/2003 | Coward |

FOREIGN PATENT DOCUMENTS

| | | |
|---|---|---|
| RU | 2014059 C1 | 6/1994 |

OTHER PUBLICATIONS

69pleasuretoys: http://69pleasuretoys.com/whipsmart-camo-green-love-handles-p-2627.html, Jul. 21, 2011.
Pipedream: http://www.pipedreamproducts.com/showdetail-12j.php?ull_Number=PD2156-23, Jul. 21, 2011.
Pipedream: http://www.pipedreamproducts.com/showdetail-20.php?Full_Number=PD3835-00, Jul. 21, 2011.
Love Handles Riding Belt—http://www.bdsmtoybox.com/browseproducts/2755A---Love-Handles-Riding-Belt.HTML, Jul. 21, 2011.
Pipedream: http://www.pipedreamproducts.com/showdetail-20.php?Full_Number=PD3849-00, Jul. 21, 2011.

*Primary Examiner* — John Lacyk
(74) *Attorney, Agent, or Firm* — Garvey, Smith, Nehrbass & North, L.L.C.; Vanessa M. D'Souza; Charles C. Garvey, Jr.

(57) ABSTRACT

An apparatus for use during sexual activities, such as sexual intercourse, comprising a belt, a means of securing the belt to a user's body, and one or more handles connected to the belt, wherein the handles extend outwardly and substantially perpendicularly from the belt and extend outwardly from the user's waist and substantially perpendicularly from the user's waist when the belt is secured around the waist of the user.

20 Claims, 17 Drawing Sheets

AMUSEMENT DEVICE

CROSS-REFERENCE TO RELATED APPLICATIONS

Priority of U.S. Provisional Patent Application Ser. No. 61/550,268, filed 21 Oct. 2011, which is incorporated herein by reference, is hereby claimed.

In the US, this is a nonprovisional patent application of U.S. Provisional Patent Application Ser. No. 61/550,268, filed 21 Oct. 2011, which is hereby incorporated herein by reference.

STATEMENT REGARDING FEDERALLY SPONSORED RESEARCH OR DEVELOPMENT

Not applicable

REFERENCE TO A "MICROFICHE APPENDIX"

Not applicable

BACKGROUND OF THE INVENTION

1. Field of the Invention

The apparatus of the present invention relates to a device for use during sexual activities, such as sexual intercourse. More particularly, the present invention relates to a sexual aid belt with handles worn on one participant's waist and employed during sexual activities, such as sexual intercourse, enabling another participant to control the participant wearing the device and providing enhanced control of motion and angle of sexual positions, as well as stabilizing the participant wearing the device. The device can be used in multiple sexual positions and can dramatically enhance the sexual experience.

2. General Background of the Invention

There are various devices created for use in enhancing sexual activities between partners. In the art there are devices for use during sexual activities, such as sexual intercourse, to enhance the sexual experience. Examples of possibly related patents directed to such devices are listed in the following table. The following US Patents are incorporated herein by reference:

TABLE

| PAT. NO. | TITLE | ISSUE/PUB DATE MM-DD-YYYY |
|---|---|---|
| 4,343,299 | Stabilizing apparatus for male and female partners | Aug. 10, 1982 |
| 4,430,990 | Body harness device | Feb. 14, 1984 |
| 4,524,760 | Sexual aid | Jun. 25, 1985 |
| 6,604,526 | Sexual aid harness | Aug. 12, 2003 |
| 2003/0145861 | Sexual Aid Harness | Aug. 07, 2003 |
| D622,031 | Belt | Aug. 24, 2010 |

U.S. Pat. No. 4,524,760 discloses a device for wearing during sexual intercourse including a waist band which can be fastened around a person's waist and leg bands for fastening around that person's thighs, the waist and thigh bands being connected together by nonextensible material providing a portion for gripping by one's partner whereby the partner can control the wearer's hip movements, as desired.

U.S. Pat. No. 6,604,526 discloses a sexual harness which provides grasping means provided in between the layers of the harness in order for the rear participant of a coital tandem to be better able to control the pelvic movements of the wearer of the device. This device can also include shoulder straps and leg stirrups for additional attachment to a user.

U.S. Pat. No. 4,430,990 discloses a body harness device which includes a pair of elongated straps each of which has a foot engagable stirrup thereon and terminates at an upper end in a shoulder strap arrangement such that in use the elongated straps are disposed generally lengthwise of the wearer and a force applied longitudinally downwardly on either of the elongated straps is distributed between both shoulders of the wearer while facilitating a desired relation between the marital partners.

US Publication No. 2003/0145861 discloses a sexual harness which provides increased stimulation, comfort and support for both participants involved in tandem coitus, and which is of a construction utilizing a plurality of layers, one of which is of an elastically yieldingly compressible material having good deformation memory properties. The device further includes a pair of shoulder straps and leg stirrups for additional attachment to the user.

The following references are incorporated herein by reference:

http://69pleasuretoys.com/whipsmart-camo-green-love-handles-p-2627.html http://www.pipedreamproducts.com/showdetail-12j.php?Full_Number=PD2156-23 http://www.pipedreamproducts.com/showdetail-20.php?Full_Number=PD3835-00 http://www.sub-shop.com/browseproducts/2755A—Love-Handles-Riding-Belt.HTML http://www.pipedreamproducts.com/showdetail-20.php?Full_Number=PD3849-00

BRIEF SUMMARY OF THE INVENTION

The present invention includes an apparatus for use during sexual activities, comprising a belt, a means of securing the belt to a user's body, and one or more handles connected to the belt, wherein the handles extend outwardly and substantially perpendicularly from the belt and extend outwardly from the user's waist and substantially perpendicularly from the user's waist when the belt is secured around the waist of the user.

Preferably, the handles are located on the belt near the user's hips when the belt is secured around the waist of the user.

Preferably, the handles extend at about a 90 degree angle from the belt.

Preferably, the apparatus further comprises a lining material secured to the inner side of the belt.

Optionally, the belt is secured to the user with a buckle and strap.

Optionally, the belt is secured to the user with velcro.

Optionally, the handles are connected to the belt with a nut and a bolt.

Optionally, the handles are connected to the belt with screws.

Preferably, the handles are located on the sides of the user's body.

Preferably, the handles are made of pipes.

Preferably, the apparatus further comprises a gripping material on the handles.

Optionally, the gripping material is a grip tape.

Optionally, the gripping material is leather.

Preferably, there are two handles.

Preferably, the two handles are on opposite ends of the belt when the belt is secured around the waist of the user.

Preferably, the handles are rigidly secured to the belt.

Preferably, the handles are on opposite sides of the user's waist when the belt is secured around the waist of the user.

Preferably, the belt encircles the user's waist.

Optionally, the handles are made of metal.

Optionally, the handles are made of plastic.

Optionally, the handles are made of rubber.

The present invention includes an apparatus for use during sexual activities, comprising a belt having an inner surface that engages the torso of a wearer and an outer surface; fastening means of securing the belt to a wearer's body wherein the belt encircles the wearer's torso, the wearer's body having a central longitudinal axis, a left side and a right side; a pair of elongated handles connected to the outer surface of the belt and extending laterally away from the outer surface at spaced apart, opposing positions, each handle extending away from the central longitudinal axis, one said handle being on the said left side, the other handle being on the right side; wherein the handles are generally horizontally positioned when the wearer's central longitudinal axis is vertical; and each handle having a gripping surface that enables a person's hand to grip the handle with fingers and thumb.

Preferably, the handles are located on the belt near the wearer's hips when the belt is secured around the wearer's torso.

Preferably, the handles each extend at about 90 degrees from the belt outer surface.

Preferably, the invention further comprises a lining material secured to the inner surface of the belt.

Preferably, the fastening means is a buckle and strap.

Preferably, each handle is connected to the belt with a connector that extends through the belt and into the handle.

Preferably, the connector has a central axis that aligns generally with the handle.

Preferably, the handles are generally cylindrically shaped.

Preferably, the invention further comprises a layer of gripping material on each handle.

Preferably, the layer of gripping material is grip tape layer.

Preferably, each handle has a handle central axis and the handle axes form an angle of between about 90 and 180 degrees.

Preferably, the handle axes form an angle that is about 180 degrees.

Preferably, the handles are rigidly secured to the belt.

Preferably, each handle is between about 4 inches and 6 inches (10 cm and 15 cm) long and between about ½ inches and 1¼ inches (12 mm and 32 mm) in thickness or diameter.

Optionally, the fastening means includes a hook-and-loop fastener.

Optionally, the fasteners are screws.

Optionally, the handles are of metallic material.

Optionally, the handles are of a plastic material.

Optionally, the handles are of a rubber material.

Preferably, the layer of gripping material is a layer of leather.

The present invention includes an apparatus for use during sexual activities, comprising a belt having an inner surface that engages the torso of a wearer and an outer surface; fastening means of securing the belt to a wearer's body wherein the belt encircles the wearer's torso, the wearer's body having a sagittal plane; and a pair of elongated handles connected to the outer surface of the belt and extending laterally away from the outer surface at spaced apart, opposing positions, each handle extending away from the sagittal plane; wherein the handles are generally horizontally positioned when the wearer's sagittal plane is vertical; and each handle having a gripping surface that enables a person's hand to grip the handle with fingers and thumb.

The present invention includes an apparatus for use during sexual activities, comprising a belt, a means of securing the belt to a user's body, the user's body having a sagittal plane, and one or more handles connected to the belt, wherein the handles extend outwardly from the belt and at an acute angle or about an acute angle to the sagittal plane when the belt is secured around the waist of the user.

Preferably, the angle can be about 60-90 degrees from the sagittal plane, more preferably about 70-90 degrees, still more preferably about 75-90 degrees, even more preferably about 85-90 degrees, and most preferably, the angle can be about 90 degrees.

Preferably, each handle has a central axis and the handle axes can form an obtuse angle or about an obtuse angle with one another.

BRIEF DESCRIPTION OF THE DRAWINGS

For a further understanding of the nature, objects, and advantages of the present invention, reference should be had to the following detailed description, read in conjunction with the following drawings, wherein like reference numerals denote like elements and wherein.

DETAILED DESCRIPTION OF THE INVENTION

Figure 1:
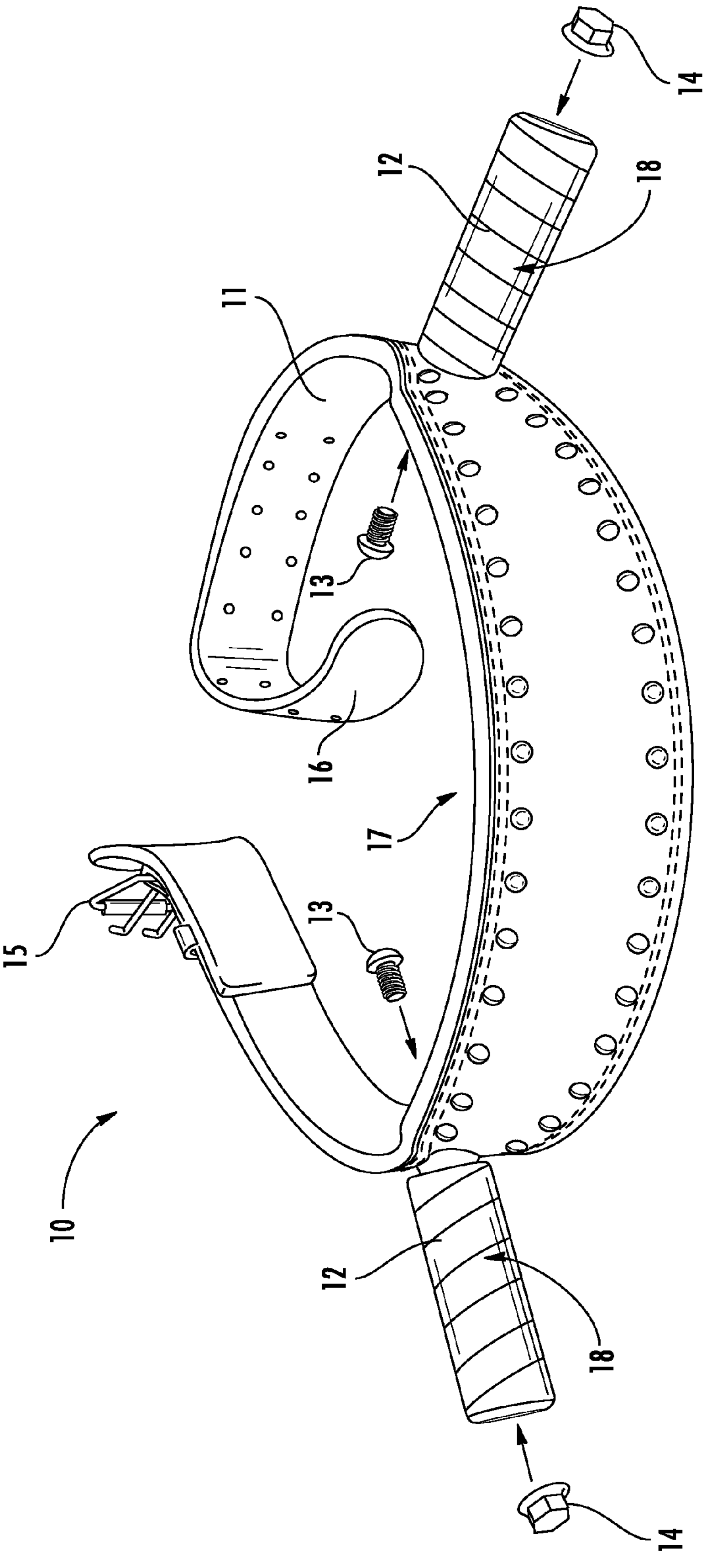
FIG. 1 is a perspective view of a preferred embodiment of the present invention.
Figure 2:
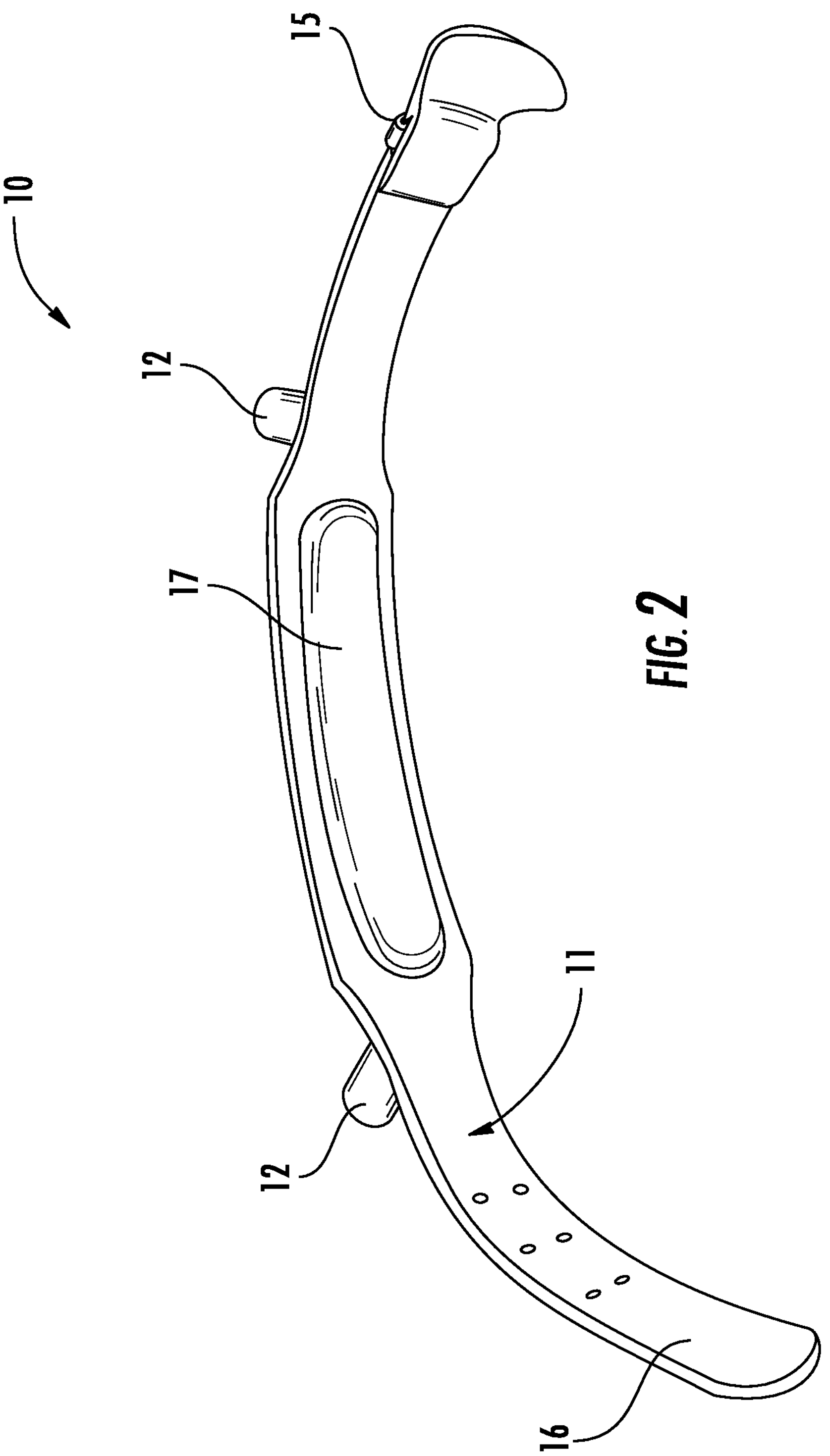
FIG. 2 is a perspective view of a preferred embodiment of the present invention.
Figure 3:
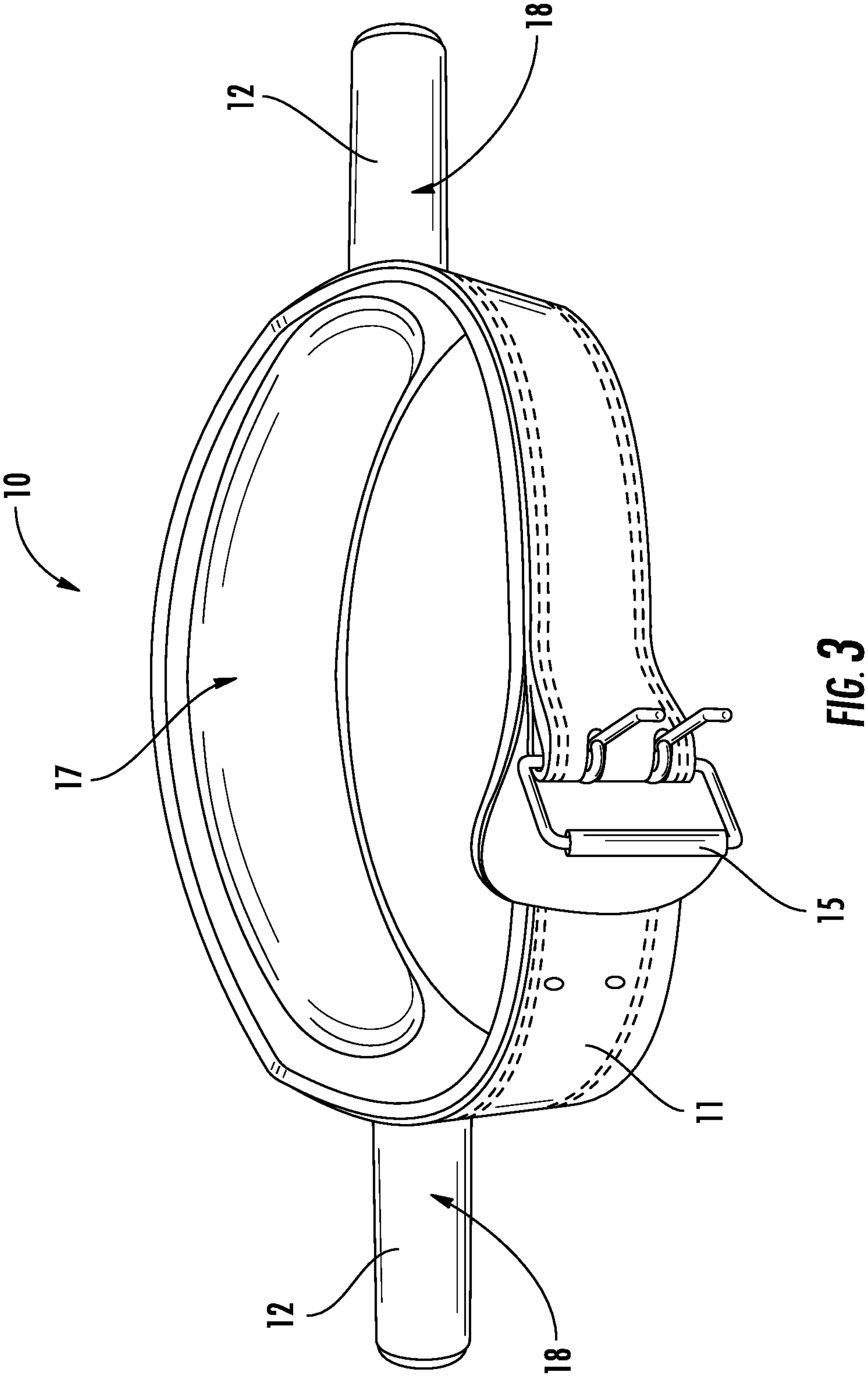
FIG. 3 is a perspective view of a preferred embodiment of the present invention.
Figure 4:
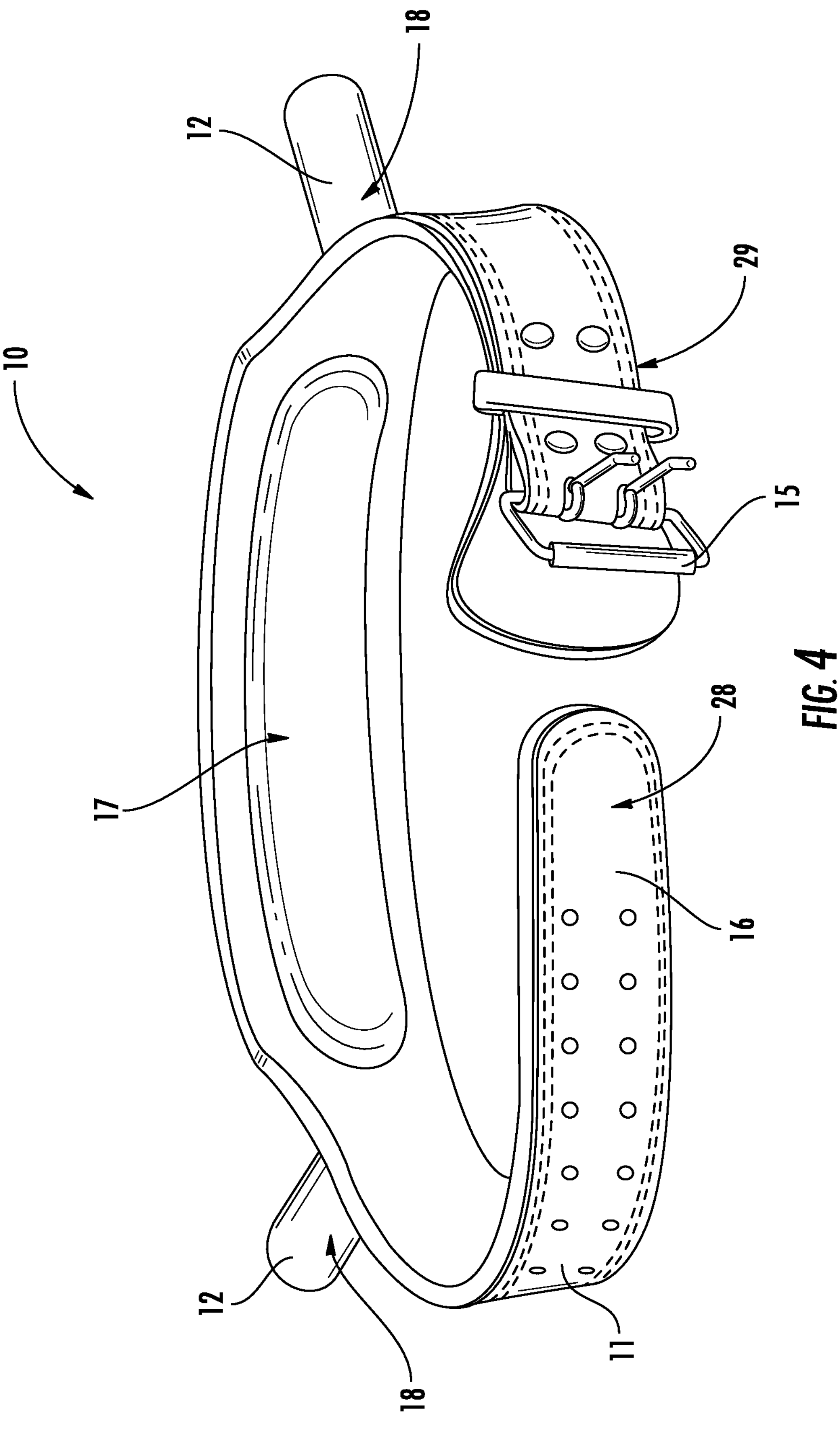
FIG. 4 is a perspective view of a preferred embodiment of the present invention.
Figure 5:
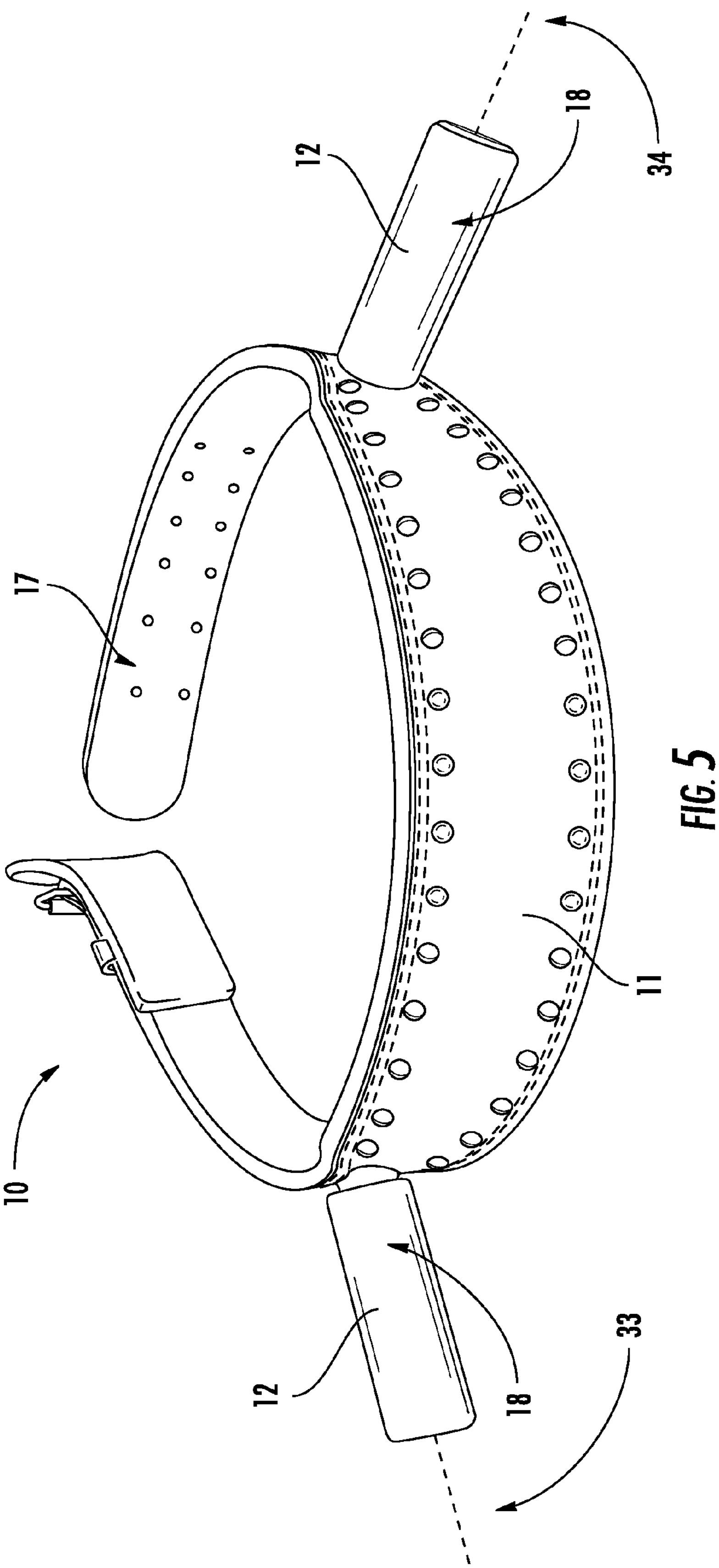
FIG. 5 is a perspective view of a preferred embodiment of the present invention.
Figure 6:
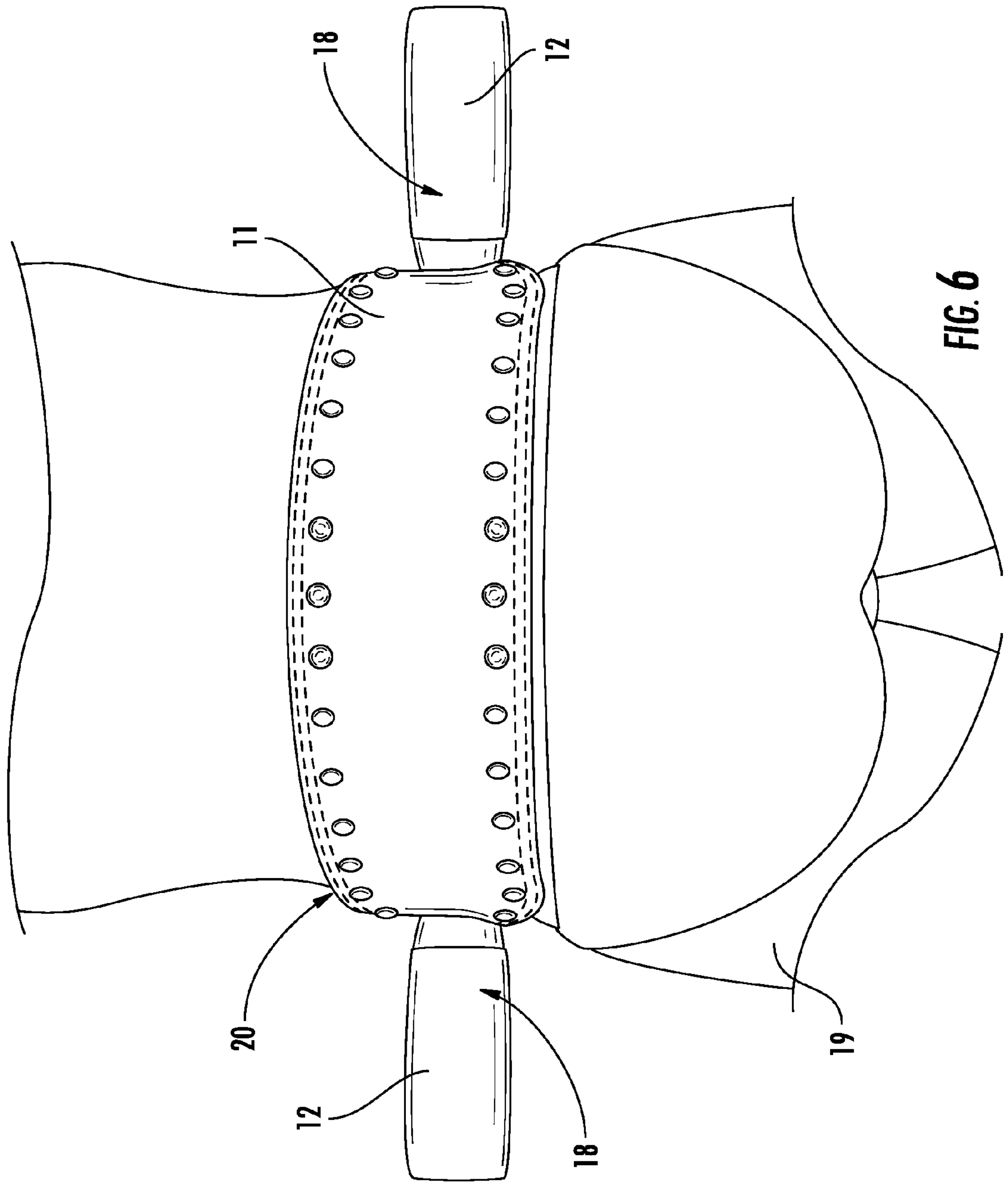
FIG. 6 is a back perspective view of a preferred embodiment of the present invention in use on a user.
Figure 7:
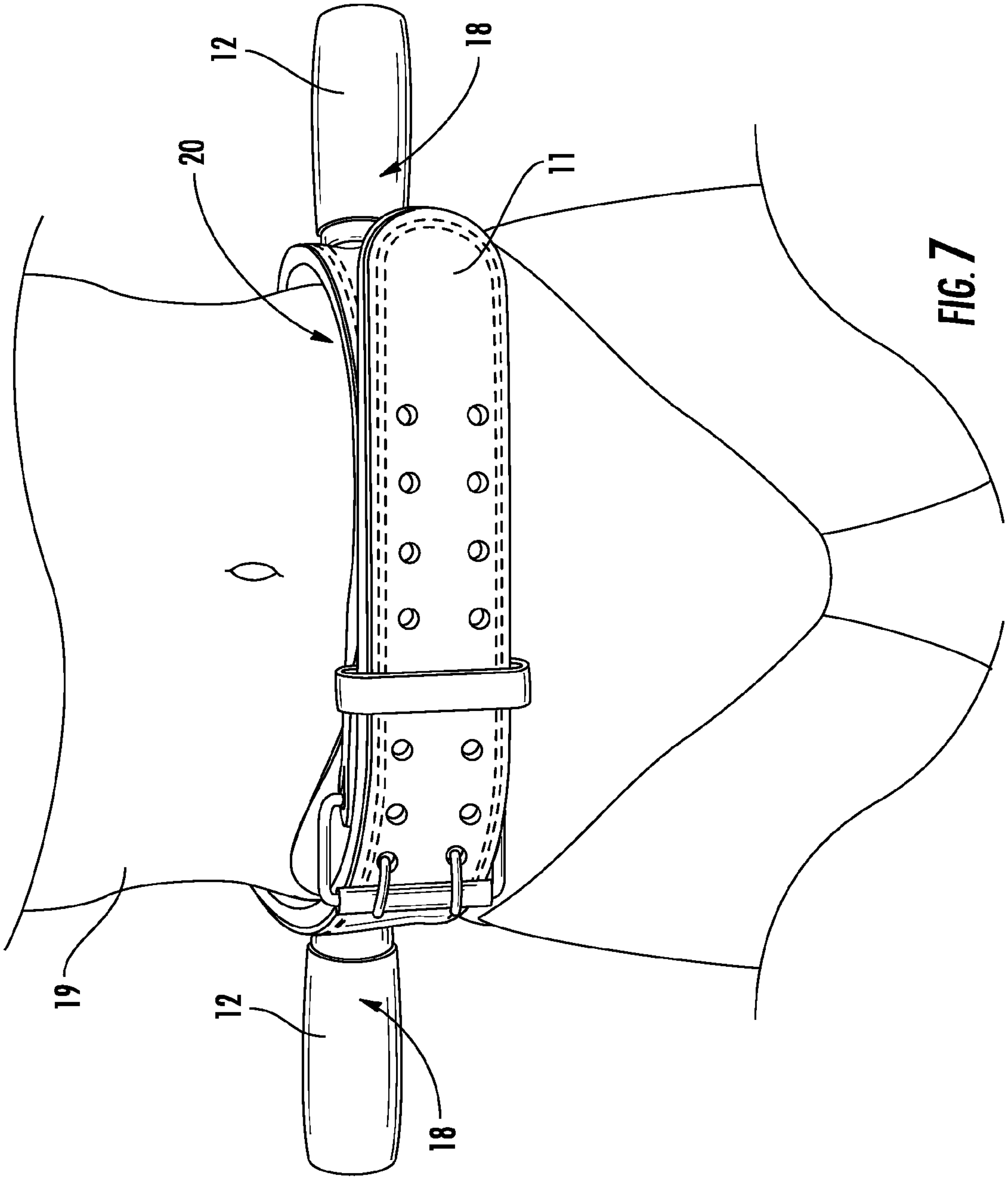
FIG. 7 is a front perspective view of a preferred embodiment of the present invention in use on a user.
Figure 8:
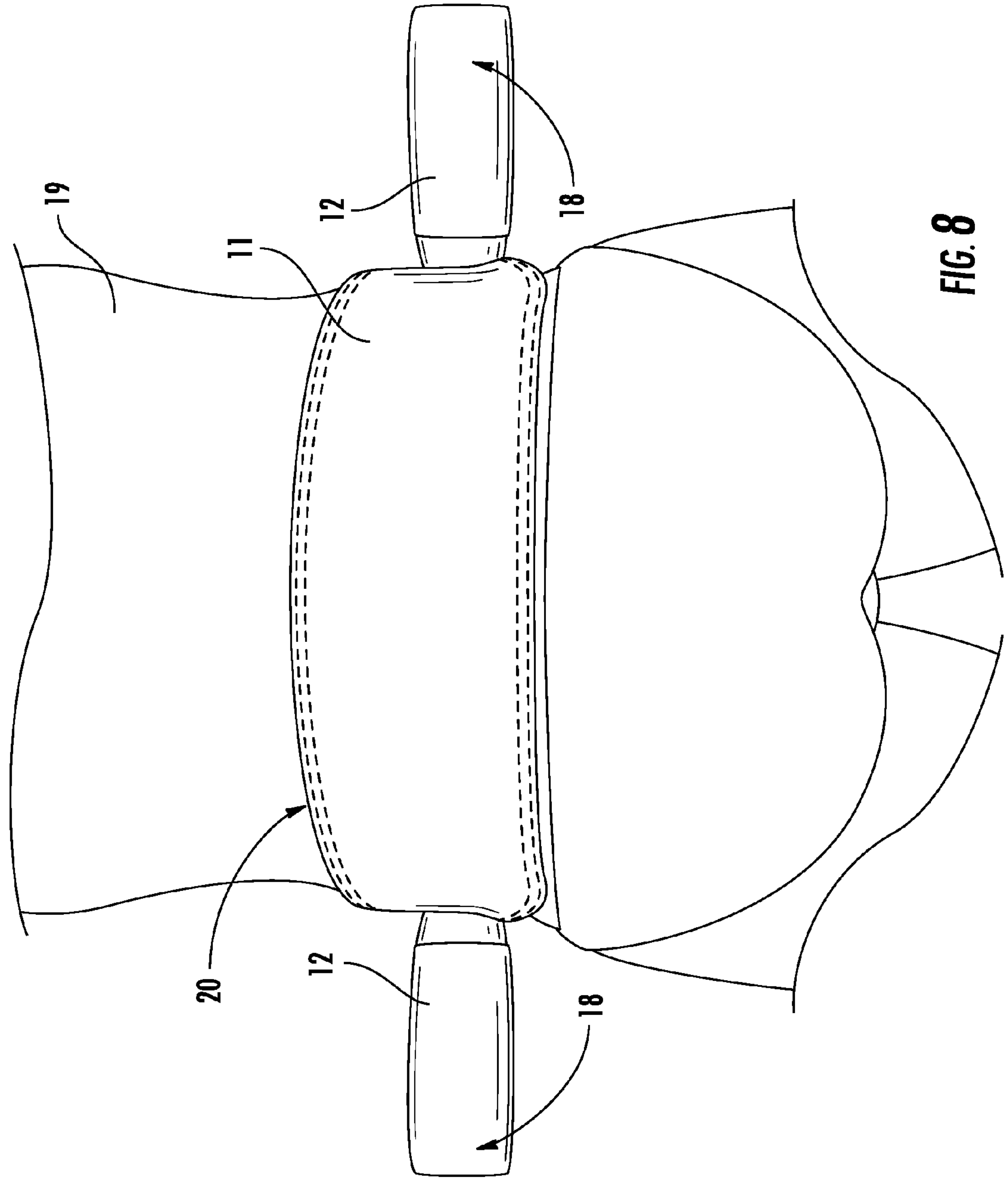
FIG. 8 is a back perspective view of a preferred embodiment of the present invention in use on a user.

Preferred embodiments of the apparatus of the present invention are seen in FIGS. 1-17. The present invention includes a device 10 that can be used during sexual activities, such as sexual intercourse, whereby one partner can control the motion and angle of sexual positions, as well as stabilizing the other partner wearing the device 10. Device 10 includes a belt 11 and handles or bars 12 attached to the belt 11. As seen in FIGS. 6-15, the belt 11 is secured to the waist portion or torso 20 of a user 19 and can encircle a user's entire waist or torso 20. Belt 11 has ends 28, 29 that can be fastened together by a securing or fastening means and adjusted to the user's waist size. The securing or fastening means, such as a buckle 15 and strap 16 (see FIGS. 4, 7 and 15), hook-and-loop fasteners (such as those sold under the trademark Velcro), double-ring fastener, buttons, or tie-string (i.e., laced) can be used to secure the belt to a user 19. The inner side of the belt 11 can be lined with a material 17, such as padding, soft lining, fur, foam, or memory foam that provides comfort for the wearer 19 and can provide a more secure hold of the belt 11 to the wearer's body.

Belt 11 can be made of for example leather or vinyl, though other suitable materials will be apparent to those of ordinary skill in the art. The belt 11 width can be about 3"-6" (7 cm-15 cm), preferably about 4" (10 cm), and the belt length can be about 37"-72" (94 cm-183 cm). The handles or bars 12 are connected to belt 11 by an attachment means or connector, such as a nut 14 and bolt 13 (see FIG. 1), though they could be connected instead by screws. The nuts 14 can be about ½"-¾" (12 mm-19 mm), preferably ⅜" (9.5 mm) threaded nuts. The bolts 13 can be about ½"-¾" (12 mm-19 mm), preferably ⅜" (9.5 mm) carriage bolts.

Handles 12 are attached to belt 11 and can extend outwardly and substantially perpendicularly from belt 11 and can extend outwardly from the user's waist or torso 20 and substantially perpendicularly from the user's torso 20 when the belt 11 is secured around the waist 20 of the user, as seen in FIGS. 6-15. For instance, the handles 12 can extend at about a 90 degree angle to the belt 11. One or more handles 12 can be attached to the belt 11 at a location near a hip of a user 19. There can be two handles 12 on opposite ends of the belt 11 when the belt is secured around the waist 20 of the user 19.

Each handle has a handle central axis 33, 34 and the handles axes 33, 34 can form an angle of about 90 to 180 degrees. Preferably, the handle axes 33, 34 can form an angle that is about 180 degrees (see FIG. 4). Handles 12 can be located on opposite sides of the user's waist 20 when the belt 11 is secured around the waist or torso 20 of the user 19 (see FIGS. 6, 7, 13).

Figure 9:
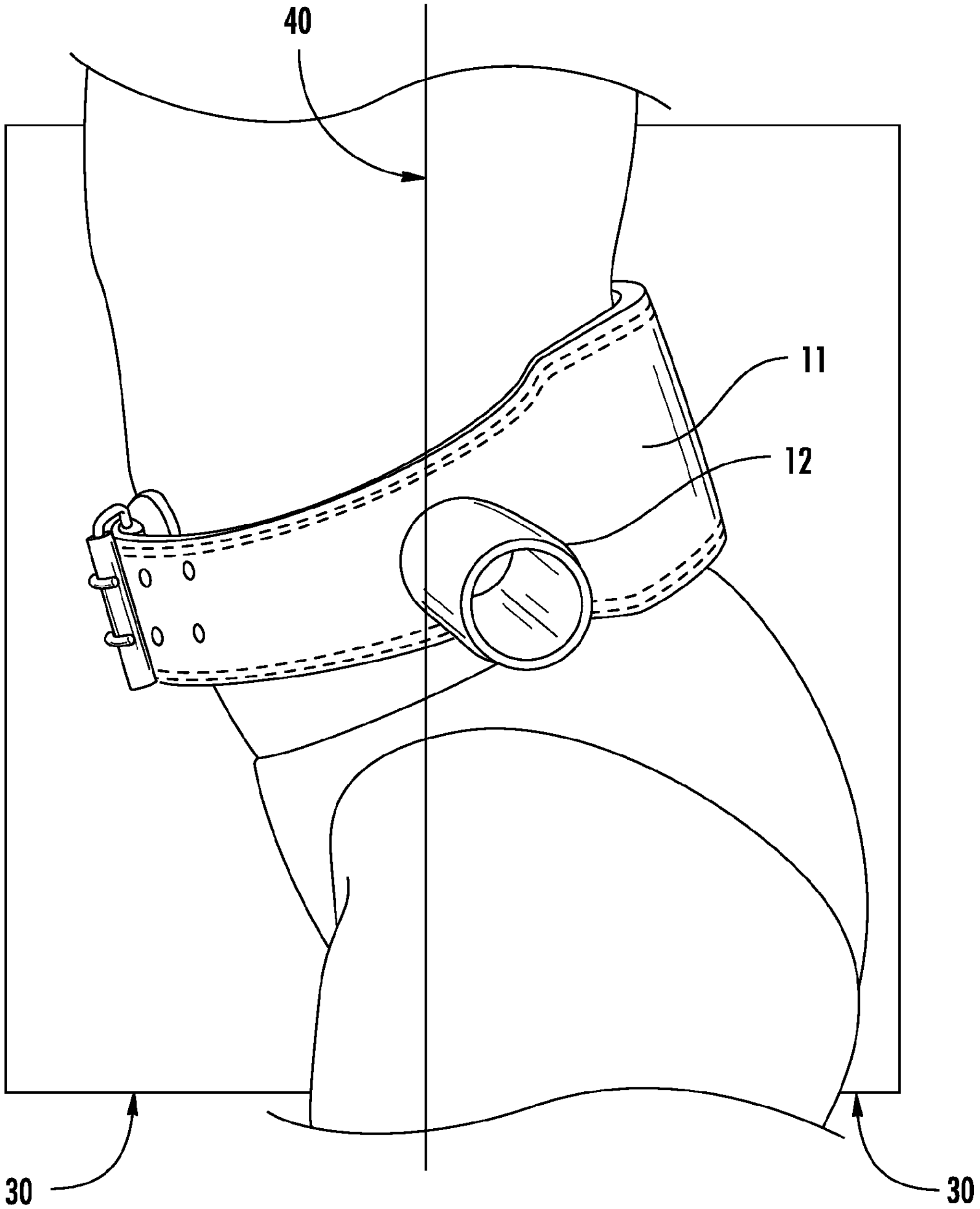
FIG. 9 is a side perspective view of a preferred embodiment of the present invention in use on a user.
Figure 10:
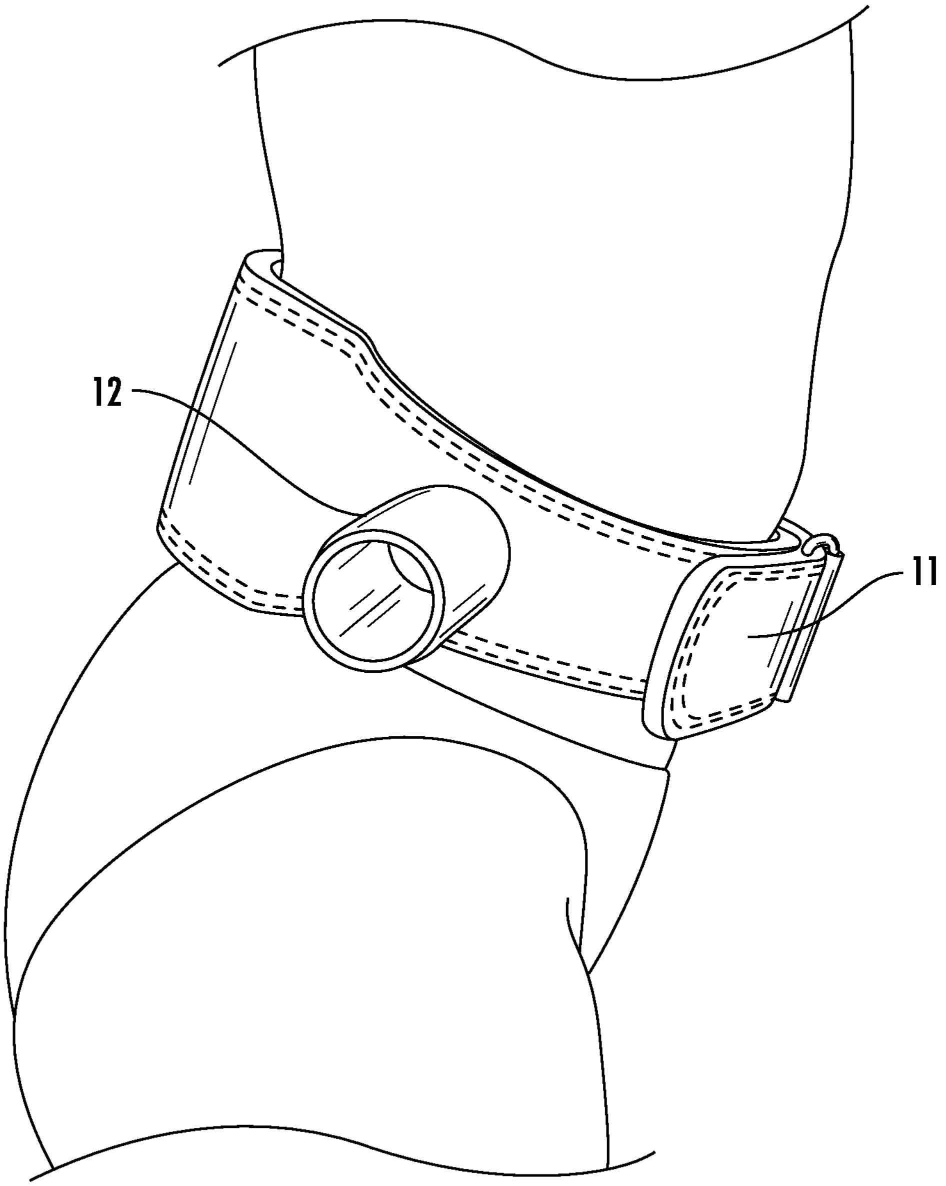
FIG. 10 is a side perspective view of a preferred embodiment of the present invention in use on a user.
Figure 11:
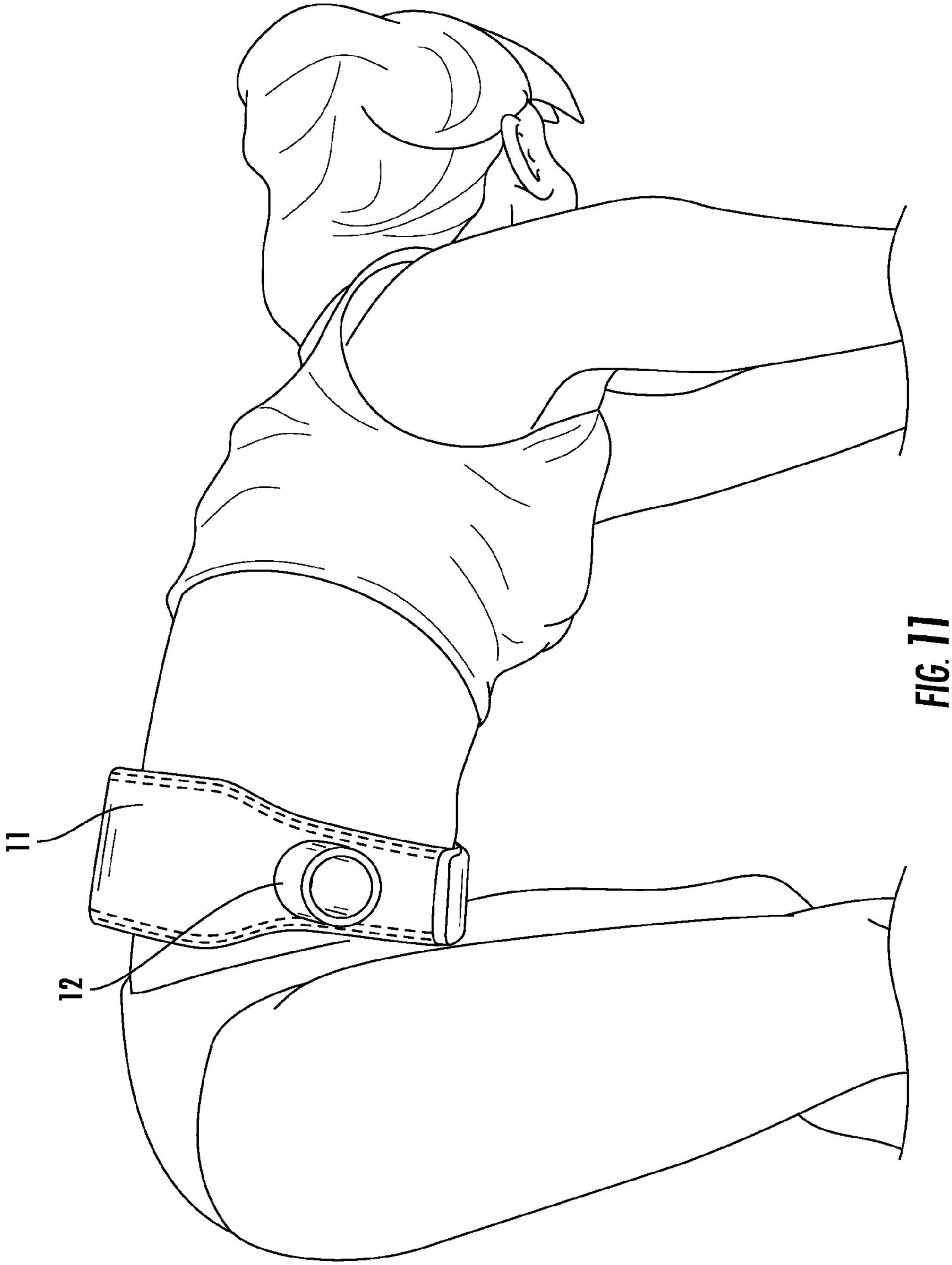
FIG. 11 is a side perspective view of a preferred embodiment of the present invention in use on a user.
Figure 12:
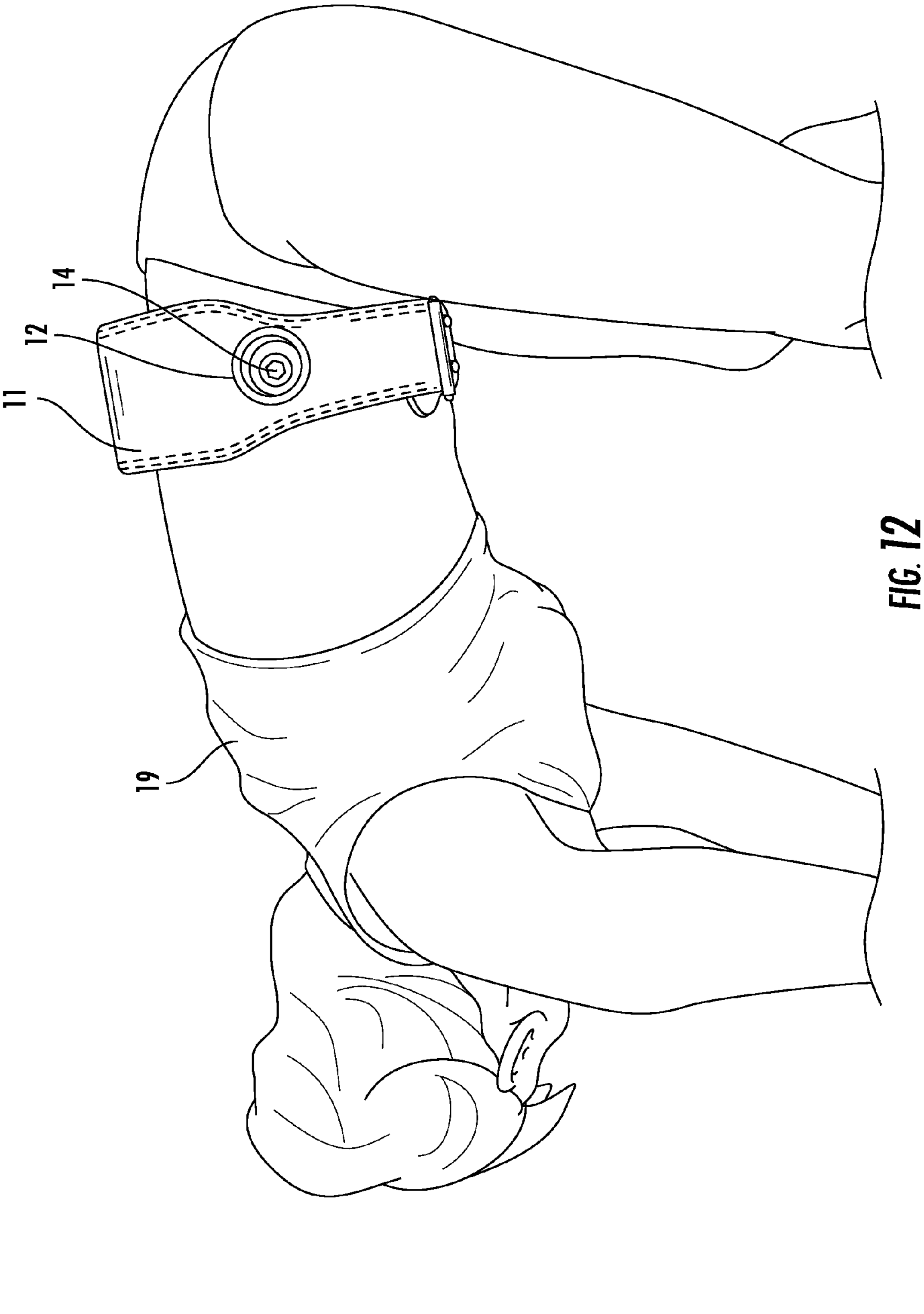
FIG. 12 is a side perspective view of a preferred embodiment of the present invention in use on a user.
Figure 13:
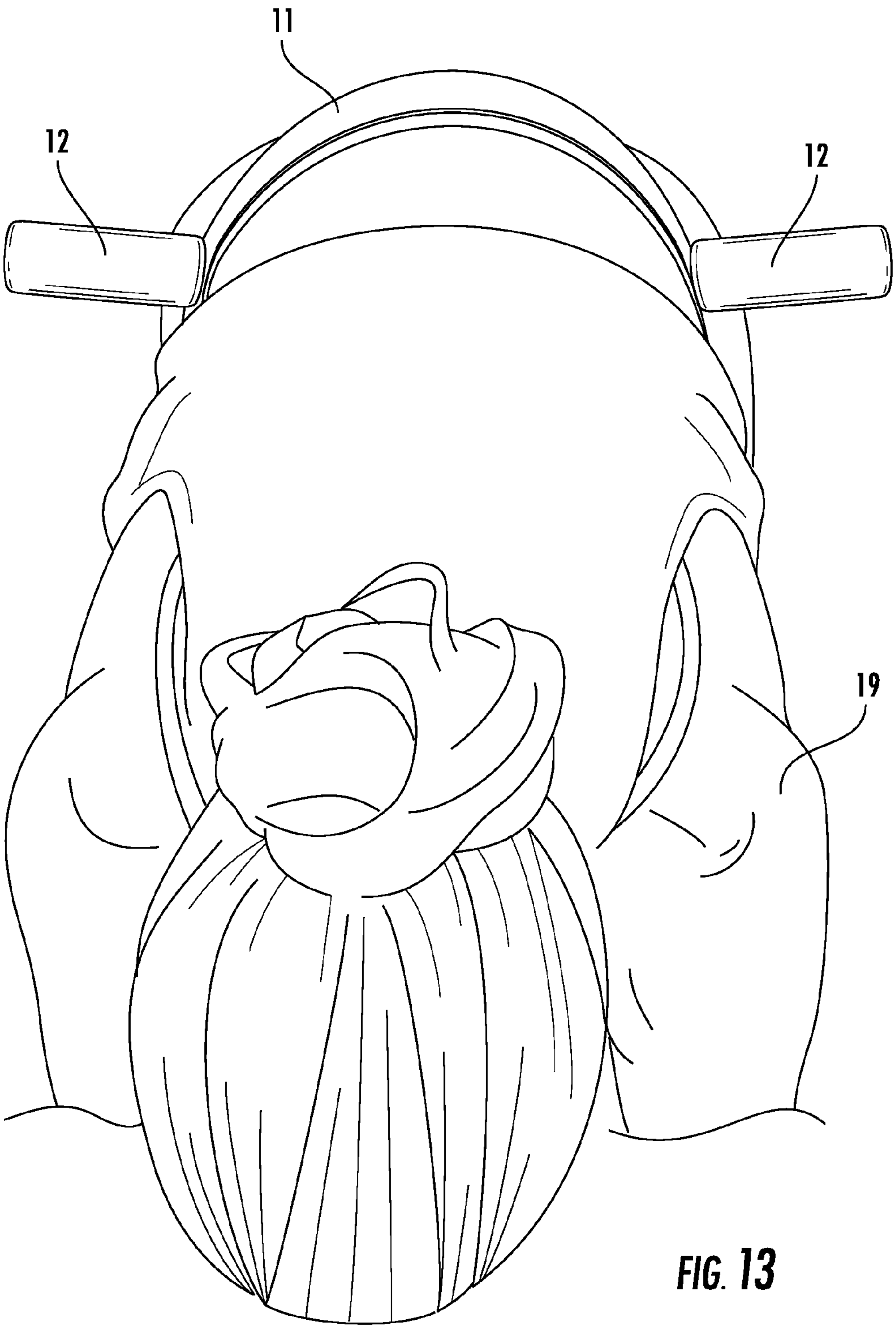
FIG. 13 is a front perspective view of a preferred embodiment of the present invention in use on a user.
Figure 14:
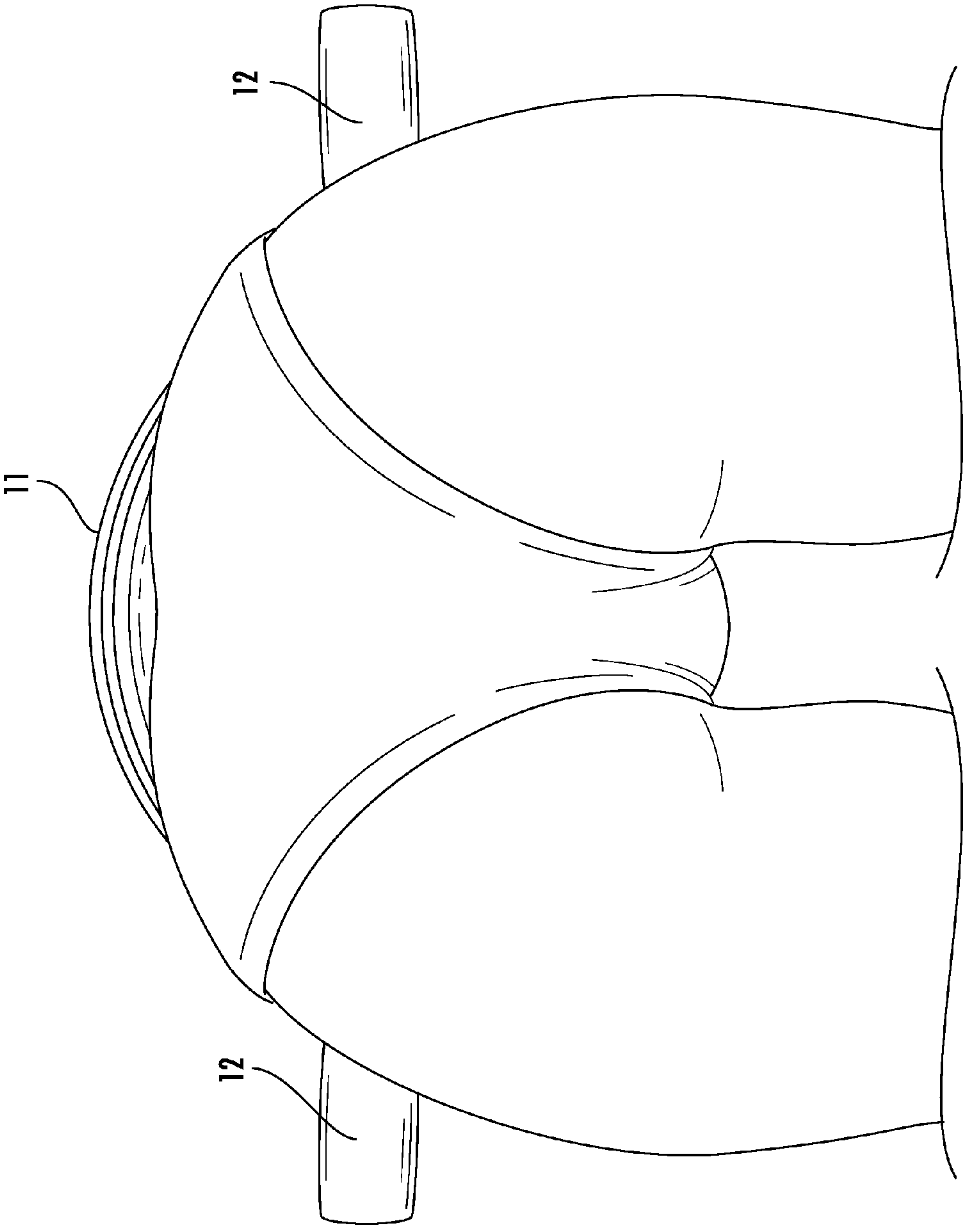
FIG. 14 is a back perspective view of a preferred embodiment of the present invention in use on a user.
Figure 15:
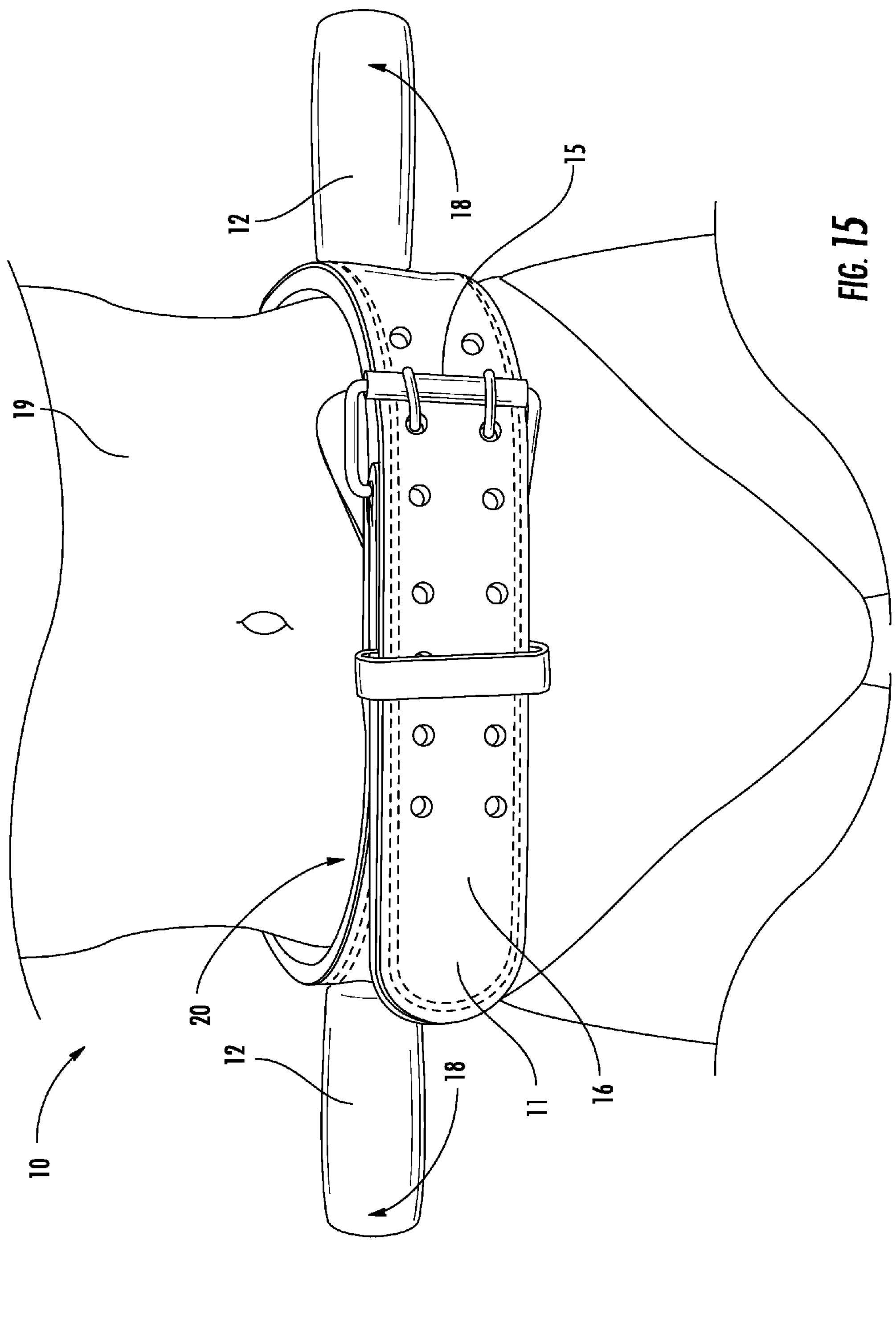
FIG. 15 is a front perspective view of a preferred embodiment of the present invention in use on a user.
Figure 16:
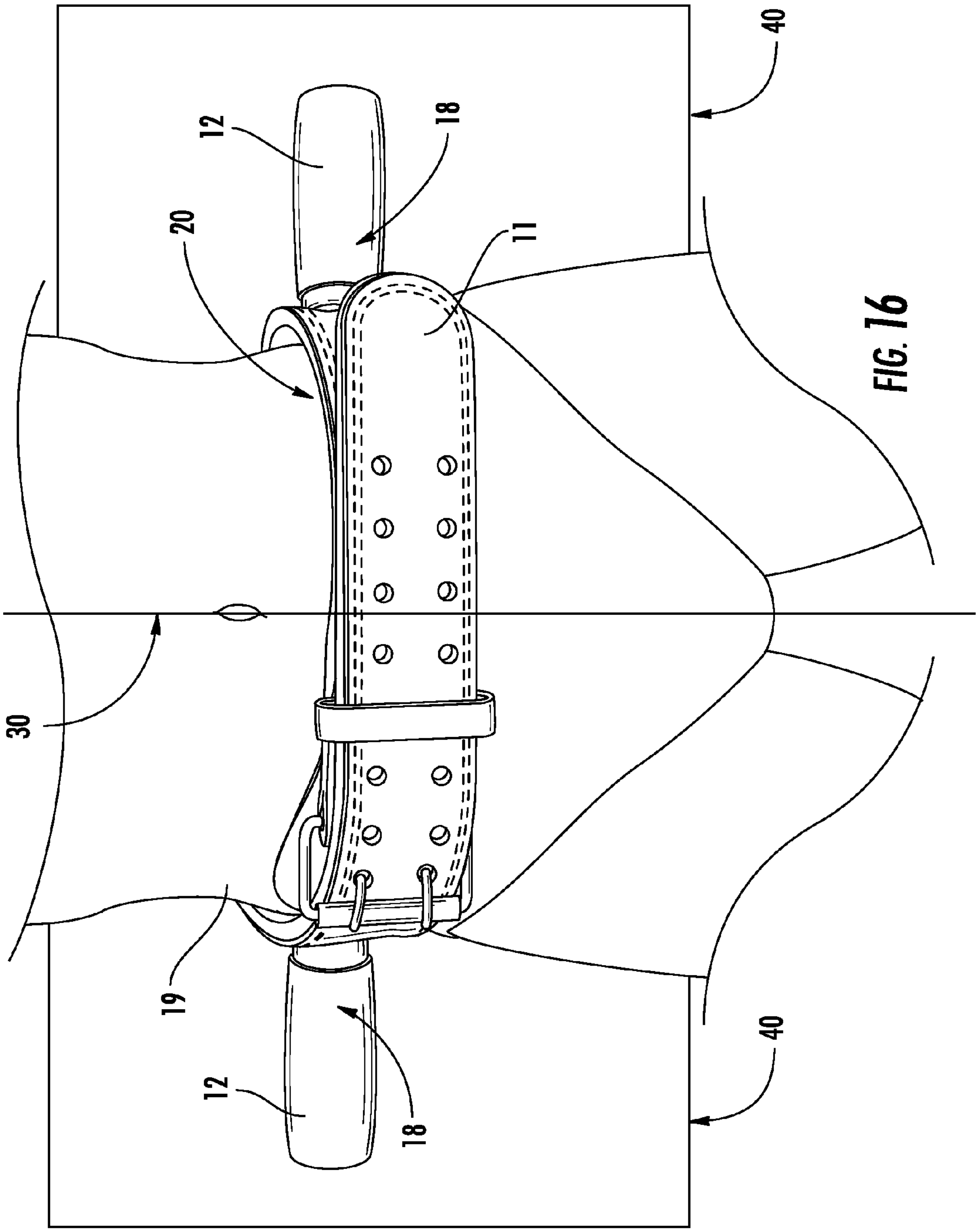
FIG. 16 is a front perspective view of a preferred embodiment of the present invention in use on a user.

The wearer's body has a central longitudinal axis and a sagittal plane 30, left and right sides and a coronal plane 40 (see FIGS. 9 and 16). The sagittal plane 30 is defined as a vertical plane which passes from front to rear of a body and dividing the body into generally symmetrical right and left halves. The coronal plane 40 is defined as a vertical plane that divides the body into two halves, front and back sections, in an imaginary line that cuts through both shoulders. Handle axes 33, 34 can lie within or near the coronal plane 40. The handle axes 33, 34 can be substantially perpendicular to the sagittal plane and substantially parallel to the coronal plane. Handles 12 can extend laterally away from the outer surface of the belt 11 and can extend away from the central longitudinal axis or sagittal plane 30 of user's body, one handle being on the left side and the other handle being on the right side. The handles are generally horizontally positioned when the user's central longitudinal axis or sagittal plane 30 is vertical. The handles 12 can be rigidly secured to the belt 11 with a connector or attachment means that can extend through the belt into the handle. The connector has a central axis that aligns generally with the handle 12.

The present invention includes an apparatus 10 for use during sexual activities, comprising a belt 11, a means of securing the belt to a user's body, the user's body having a sagittal plane 30, and one or more handles 12 connected to the belt 11, wherein the handles 12 extend outwardly from the belt 11 and at an acute angle or about an acute angle to the sagittal plane 30 of the user's body when the belt is secured around the waist 20 of the user 19. The angle can be about 90 degrees. Each handle has a central axis 33, 34 and the handle axes can form an obtuse angle or about an obtuse angle.

Handles or bars 12 can be made from rubber, plastic or metal material, and can be round or pipe-style shaped and about ½ inches-1¼ inches (12 mm-32 mm) in diameter and about 4 inches-6 inches (10 cm-15 cm) long. Other shapes for the handles 12 could be substantially cylindrical, and the handles could have ornamental shapes such as body parts, such as for example penises. The handles 12 are preferably covered with a layer of gripping material 18, such as grip tape or leather. The gripping material 18 assists a participant to more securingly hold and control the other user 19 wearing the belt 11.

Handles 12 can also be detachable from belt 11. Handles 12 can be made of material that can glow in the dark or covered with material that can glow in the dark. Hand cuffs and/or tie straps can be attached to belt 11. The cuffs can be made of metal, plastic, or other suitable materials and can optionally be covered with fur or other soft material. The device 10 can be equipped with a digital audio player, such as an MP3 player or the like, and speakers.

The ends of handles 12 can be capped with a rubber plug. Each rubber plug can be removed from handle 12. The rubber plug can have the following accessories attached to it: feather, whip, butt plug. These accessories can rest within the handle when the rubber plug is connected to the handle.

The apparatus of the present invention is preferably used as a sex belt device 10. The placement of the handles 12 positioned on the sides of the belt 11 act as handlebars. The belt 11 can be used in multiple sexual positions and can dramatically enhance the sexual experience. The belt 11 can be used for complete control of motion and angle, as well as total control of the pelvis. The inner side of the belt 11 can have padding or lining 17 to provide comfort for the wearer 19. The handles or bars 12 can be connected to the belt with a nut 14 and bolt 13. The bolts 13 can be ⅜" (9.5 mm) carriage bolts. The nuts 14 can be ⅜" (9.5 mm) threaded nuts. The nut 14 and bolt 13 connection provides heavy-duty strength.

Figure 17:
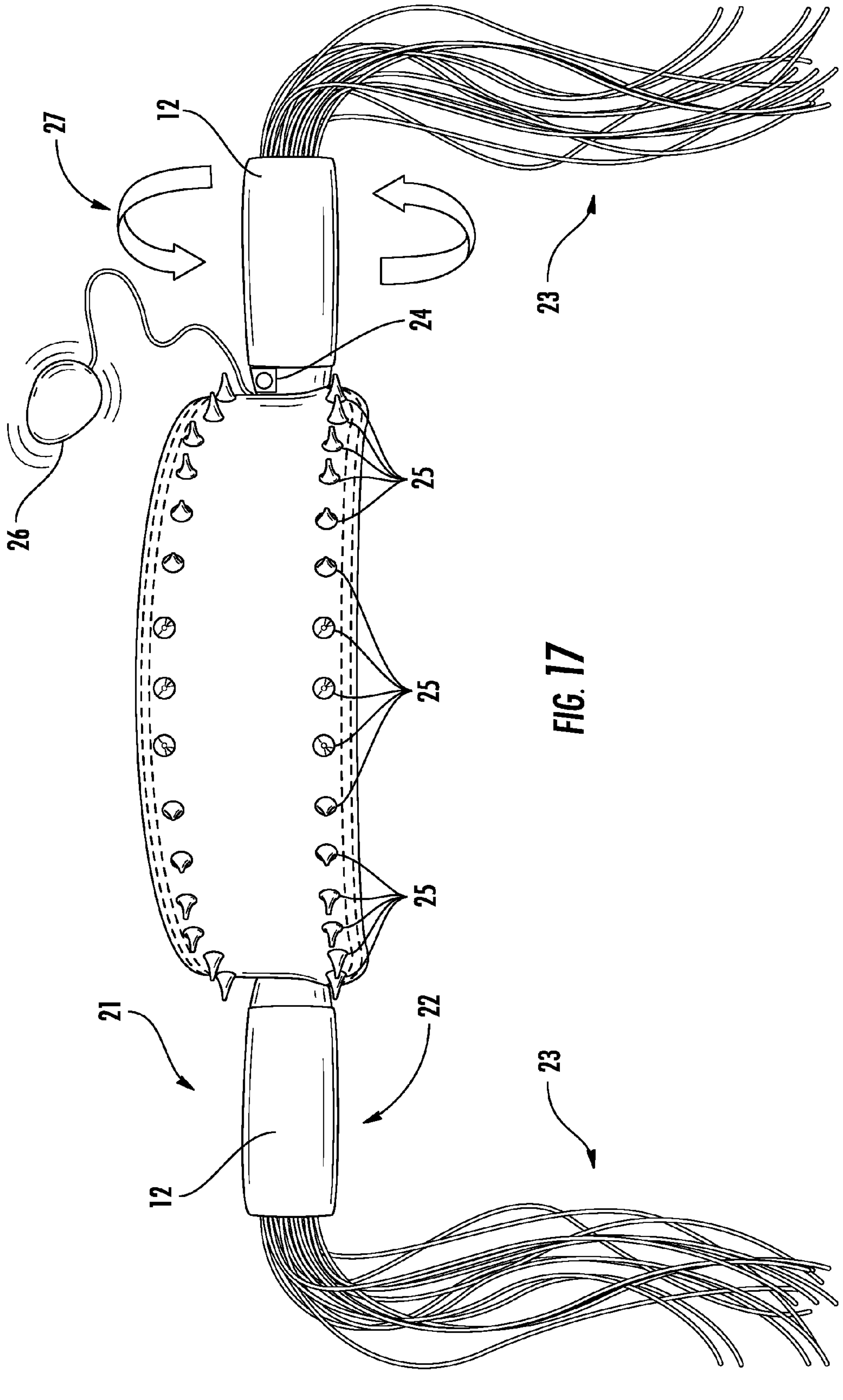
FIG. 17 is a perspective view of a preferred embodiment of the present invention.

As seen in FIG. 17, the present invention can include tassels 23 hanging from the handles or bars 12. The present invention can include a vibrating egg or vibrator 26 that can be used or applied by the user 19 and controlled by twisting the throttle 27 of a handle or bar 12, preferably on the right side, or by a push button 24, preferably located near the handle or bar 12. Batteries can be stored inside the handle or bar 12. Metal spikes 25 can be applied to the belt, as seen in FIG. 17.

Parts List

The following is a list of suitable parts and materials for the various elements of the preferred embodiment of the present invention.

| Parts Number | Description |
|---|---|
| 10 | belt device |
| 11 | belt |
| 12 | handle/bar |
| 13 | bolt |
| 14 | nut |
| 15 | buckle |
| 16 | strap |
| 17 | inner lining material |

-continued

| Parts Number | Description |
|---|---|
| 18 | grip material |
| 19 | user/wearer |
| 20 | user's waist/torso |
| 21 | motor grips |
| 22 | leather wrap |
| 23 | tassel |
| 24 | push button |
| 25 | metal spike |
| 26 | vibrating egg/vibrator |
| 27 | twist throttle |
| 28 | end of belt 11 |
| 29 | end of belt 11 |
| 30 | sagittal plane |
| 33 | handle axis |
| 34 | handle axis |
| 40 | coronal plane |

All measurements disclosed herein are at standard temperature and pressure, at sea level on Earth, unless indicated otherwise. All materials used or intended to be used in a human being are biocompatible, unless indicated otherwise.

The foregoing embodiments are presented by way of example only; the scope of the present invention is to be limited only by the following claims.

The invention claimed is:

1. An apparatus for use during sexual activities, comprising:

a) a belt having an inner surface that engages the torso of a wearer and an outer surface;

b) fastening means of securing the belt to a user's body wherein the belt encircles the wearer's torso, the user's body having a central longitudinal axis, a left side and a right side; and c) a pair of elongated handles connected to the outer surface of the belt and extending laterally away from the outer surface at spaced apart, opposing positions, each handle extending away from the central longitudinal axis, one said handle being on the said left side, the other handle being on the right side;

d) wherein the handles are generally horizontally positioned when the wearer's central longitudinal axis is vertical; and e) each handle having a gripping surface that enables a person's hand to grip the handle with fingers and thumb.

2. The apparatus or claim 1, wherein the handles are located on the belt near the wearer's hips when the belt is secured around the wearer's torso.

3. The apparatus of claim 1, wherein the handles each extend at about 90 degrees from the belt outer surface.

4. The apparatus of claim 1, wherein each handle is connected to the belt with a connector that extends through the belt and into the handle.

5. The apparatus of claim 1, wherein each handle has a handle central axis and the handle axes form an angle of between about 90 and 180 degrees.

6. The apparatus of claim 5, wherein the handle axes form an angle that is about 180 degrees.

7. An apparatus for use during sexual activities, comprising:

a) a belt having an inner surface that engages the torso of a wearer and an outer surface;

b) fastening means of securing the belt to a wearer's body wherein the belt encircles the wearer's torso, the wearer's body having a sagittal plane; and c) a pair of elongated handles connected to the outer surface of the belt and extending laterally away from the outer surface at spaced apart, opposing positions, each handle extending away from the sagittal plane;

d) wherein the handles are generally horizontally positioned when the wearer's sagittal plane is vertical; and e) each handle having a gripping surface that enables a person's hand to grip the handle with fingers and thumb.

8. The apparatus or claim 7, wherein the handles are located on the belt near the wearer's hips when the belt is secured around the wearer's torso.

9. The apparatus of claim 7, wherein the handles each extend at about 90 degrees from the belt outer surface.

10. The apparatus of claim 7, wherein each handle is connected to the belt with a connector that extends through the belt and into the handle.

11. The apparatus of claim 10, wherein the connector has a central axis that aligns generally with the handle.

12. The apparatus of claim 7, wherein each handle has a handle central axis and the handle axes form an angle of between about 90 and 180 degrees.

13. The apparatus of claim 12, wherein the handle axes form an angle that is about 180 degrees.

14. An apparatus for use during sexual activities, comprising:

a) a belt;

b) a means of securing the belt to a user's body, the user's body having a sagittal plane; and c) one or more handles connected to the belt, wherein the handles extend outwardly from the belt and at an acute angle to the sagittal plane when the belt is secured around the waist of the user.

15. The apparatus of claim 14, wherein the angle is about 60-90 degrees.

16. The apparatus of claim 14, wherein the angle is about 70-90 degrees.

17. The apparatus of claim 14, wherein the angle is about 75-90 degrees.

18. The apparatus of claim 14, wherein the angle is about 85-90 degrees.

19. The apparatus of claim 14, wherein the angle is about 90 degrees.

20. The apparatus of claim 14, wherein each handle has a central axis and the handle axes form an obtuse angle with one another.

* * * * *